(12) United States Patent
Kostrzewski

(10) Patent No.: US 8,701,962 B2
(45) Date of Patent: *Apr. 22, 2014

(54) SHIPPING WEDGE WITH LOCKOUT

(71) Applicant: Covidien LP, Mansfield, MA (US)

(72) Inventor: Stanislaw Kostrzewski, Newtown, CT (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/768,169

(22) Filed: Feb. 15, 2013

(65) Prior Publication Data

US 2013/0153629 A1 Jun. 20, 2013

Related U.S. Application Data

(63) Continuation of application No. 13/051,276, filed on Mar. 18, 2011, now Pat. No. 8,397,972.

(51) Int. Cl.
*A61B 17/068* (2006.01)

(52) U.S. Cl.
USPC ..... 227/175.2; 227/19; 227/175.3; 227/176.1

(58) Field of Classification Search
USPC ............ 227/19, 175.1, 175.2, 175.3, 176.1, 227/180.1; 606/139, 219
See application file for complete search history.

(56) References Cited

U.S. PATENT DOCUMENTS

| | | |
|---|---|---|
| 3,079,606 A | 3/1963 | Bobrov et al. |
| 3,315,863 A | 4/1967 | O'Dea |
| 3,490,675 A | 1/1970 | Green et al. |
| 3,499,591 A | 3/1970 | Green |
| 4,244,372 A | 1/1981 | Kapitanov et al. |
| 4,429,695 A | 2/1984 | Green |
| 4,520,817 A | 6/1985 | Green |
| 4,576,167 A | 3/1986 | Noiles |
| 4,589,413 A | 5/1986 | Malyshev et al. |
| 4,605,001 A | 8/1986 | Rothfuss et al. |
| 4,608,981 A | 9/1986 | Rothfuss et al. |
| 4,610,383 A | 9/1986 | Rothfuss et al. |
| 4,633,861 A | 1/1987 | Chow et al. |
| 4,633,874 A | 1/1987 | Chow et al. |
| 4,664,305 A | 5/1987 | Blake et al. |
| 4,672,964 A | 6/1987 | Dee et al. |
| 4,715,520 A | 12/1987 | Roehr, Jr. et al. |
| 4,763,669 A | 8/1988 | Jaeger |
| 4,819,853 A | 4/1989 | Green |

(Continued)

FOREIGN PATENT DOCUMENTS

DE 4300307 7/1994
DE 202 17 850 1/2003

(Continued)

*Primary Examiner* — Scott A. Smith

(57) ABSTRACT

A shipping wedge for use with a surgical instrument includes a base configured to be detachably secured with a body portion of the surgical instrument, a blocking member depending from the base and engageable with a movable operative member of the surgical instrument, and a locking member depending from the base and engageable with a lockout mechanism of the surgical instrument.

17 Claims, 16 Drawing Sheets

(56) References Cited

U.S. PATENT DOCUMENTS

| | | |
|---|---|---|
| 4,863,088 A | 9/1989 | Redmond et al. |
| 4,880,015 A | 11/1989 | Nierman |
| 4,892,244 A | 1/1990 | Fox et al. |
| 4,924,864 A | 5/1990 | Danzig |
| 4,978,049 A | 12/1990 | Green |
| 4,991,764 A | 2/1991 | Mericle |
| 5,014,899 A | 5/1991 | Presty et al. |
| 5,040,715 A | 8/1991 | Green et al. |
| 5,065,929 A | 11/1991 | Schulze et al. |
| 5,071,052 A | 12/1991 | Rodak et al. |
| 5,071,430 A | 12/1991 | De Salis et al. |
| 5,074,454 A | 12/1991 | Peters |
| 5,083,695 A | 1/1992 | Foslien et al. |
| 5,104,025 A | 4/1992 | Main et al. |
| 5,111,987 A | 5/1992 | Moeinzadeh et al. |
| 5,129,570 A | 7/1992 | Schulze et al. |
| 5,141,144 A | 8/1992 | Foslien et al. |
| 5,144,942 A | 9/1992 | Decarie et al. |
| 5,152,279 A | 10/1992 | Wilk |
| 5,156,315 A | 10/1992 | Green et al. |
| 5,180,092 A | 1/1993 | Crainich |
| 5,209,747 A | 5/1993 | Knoepfler |
| 5,275,608 A | 1/1994 | Forman et al. |
| 5,282,826 A | 2/1994 | Quadri |
| 5,307,976 A | 5/1994 | Olson et al. |
| 5,312,023 A | 5/1994 | Green et al. |
| 5,318,221 A | 6/1994 | Green et al. |
| 5,326,013 A | 7/1994 | Green et al. |
| 5,330,502 A | 7/1994 | Hassler et al. |
| 5,332,142 A | 7/1994 | Robinson et al. |
| 5,350,391 A | 9/1994 | Iacovelli |
| 5,354,311 A | 10/1994 | Kambin et al. |
| 5,358,506 A | 10/1994 | Green et al. |
| 5,366,133 A | 11/1994 | Geiste |
| 5,366,477 A | 11/1994 | LeMarie, III et al. |
| 5,374,277 A | 12/1994 | Hassler |
| 5,376,095 A | 12/1994 | Ortiz |
| 5,379,933 A | 1/1995 | Green et al. |
| 5,383,888 A | 1/1995 | Zvenyatsky et al. |
| 5,389,098 A | 2/1995 | Tsuruta et al. |
| 5,397,046 A | 3/1995 | Savage et al. |
| 5,397,324 A | 3/1995 | Carroll et al. |
| 5,403,312 A | 4/1995 | Yates et al. |
| 5,413,268 A | 5/1995 | Green et al. |
| 5,415,334 A | 5/1995 | Williamson, IV et al. |
| 5,415,335 A | 5/1995 | Knodell, Jr. |
| 5,423,471 A | 6/1995 | Mastri et al. |
| 5,433,721 A | 7/1995 | Hooven et al. |
| 5,452,837 A | 9/1995 | Williamson, IV et al. |
| 5,465,895 A | 11/1995 | Knodel et al. |
| 5,467,911 A | 11/1995 | Tsuruta et al. |
| 5,474,566 A | 12/1995 | Alesi et al. |
| 5,474,571 A | 12/1995 | Lang |
| 5,484,451 A | 1/1996 | Akopov et al. |
| 5,486,185 A | 1/1996 | Freitas et al. |
| 5,487,500 A | 1/1996 | Knodel et al. |
| 5,507,426 A | 4/1996 | Young et al. |
| 5,535,935 A | 7/1996 | Vidal et al. |
| 5,551,622 A | 9/1996 | Yoon |
| 5,562,241 A | 10/1996 | Knodel et al. |
| 5,582,617 A | 12/1996 | Klieman et al. |
| 5,597,107 A | 1/1997 | Knodel et al. |
| 5,601,573 A | 2/1997 | Fogelberg et al. |
| 5,605,272 A | 2/1997 | Witt et al. |
| 5,630,539 A | 5/1997 | Plyley et al. |
| 5,634,584 A | 6/1997 | Okorocha et al. |
| 5,651,491 A | 7/1997 | Heaton et al. |
| 5,653,373 A | 8/1997 | Green et al. |
| 5,655,698 A | 8/1997 | Yoon |
| 5,662,258 A | 9/1997 | Knodel et al. |
| 5,662,259 A | 9/1997 | Yoon |
| 5,662,260 A | 9/1997 | Yoon |
| 5,673,841 A | 10/1997 | Schulze et al. |
| 5,680,982 A | 10/1997 | Schulze et al. |
| 5,681,330 A | 10/1997 | Hughett et al. |
| 5,715,988 A | 2/1998 | Palmer |
| 5,718,359 A | 2/1998 | Palmer et al. |
| 5,762,255 A | 6/1998 | Chrisman et al. |
| 5,794,834 A | 8/1998 | Hamblin et al. |
| 5,797,537 A | 8/1998 | Oberlin et al. |
| 5,800,449 A | 9/1998 | Wales |
| 5,820,009 A | 10/1998 | Melling et al. |
| 5,893,506 A | 4/1999 | Powell |
| 5,901,895 A | 5/1999 | Heaton et al. |
| 5,911,352 A | 6/1999 | Racenet et al. |
| 5,984,938 A | 11/1999 | Yoon |
| 5,988,479 A | 11/1999 | Palmer |
| 5,993,465 A | 11/1999 | Shipp et al. |
| 6,010,054 A | 1/2000 | Johnson et al. |
| 6,032,849 A | 3/2000 | Mastri et al. |
| 6,050,472 A | 4/2000 | Shibata |
| 6,079,606 A | 6/2000 | Milliman et al. |
| 6,109,500 A | 8/2000 | Alli et al. |
| 6,119,913 A | 9/2000 | Adams et al. |
| 6,131,789 A | 10/2000 | Schulze et al. |
| 6,174,309 B1 | 1/2001 | Wrublewski et al. |
| 6,241,139 B1 | 6/2001 | Milliman et al. |
| 6,241,140 B1 | 6/2001 | Adams et al. |
| 6,585,144 B2 | 7/2003 | Adams et al. |
| 6,601,749 B2 | 8/2003 | Sullivan et al. |
| 6,607,540 B1 | 8/2003 | Shipp |
| 6,755,338 B2 | 6/2004 | Hahnen et al. |
| 6,805,273 B2 | 10/2004 | Bilotti et al. |
| 6,978,921 B2 | 12/2005 | Shelton, IV et al. |
| 6,988,650 B2 | 1/2006 | Schwemberger et al. |
| 7,000,818 B2 | 2/2006 | Shelton, IV et al. |
| 7,055,730 B2 | 6/2006 | Ehrenfels et al. |
| 7,055,731 B2 | 6/2006 | Shelton, IV et al. |
| 7,134,587 B2 | 11/2006 | Schwemberger et al. |
| 7,140,527 B2 | 11/2006 | Ehrenfels et al. |
| 7,147,139 B2 | 12/2006 | Schwemberger et al. |
| 7,147,140 B2 | 12/2006 | Wukusick et al. |
| 7,204,404 B2 | 4/2007 | Nguyen et al. |
| 7,207,472 B2 | 4/2007 | Wukusick et al. |
| 7,210,609 B2 | 5/2007 | Leiboff et al. |
| 7,278,563 B1 | 10/2007 | Green |
| RE40,237 E | 4/2008 | Bilotti |
| 7,380,696 B2 | 6/2008 | Shelton, IV et al. |
| 7,407,078 B2 | 8/2008 | Shelton, IV et al. |
| 7,434,717 B2 | 10/2008 | Shelton, IV et al. |
| 7,451,904 B2 | 11/2008 | Shelton, IV |
| 7,464,849 B2 | 12/2008 | Shelton, IV et al. |
| 7,503,474 B2 | 3/2009 | Hillstead et al. |
| 7,568,604 B2 | 8/2009 | Ehrenfels et al. |
| 7,780,055 B2 | 8/2010 | Scirica et al. |
| 8,225,979 B2 | 7/2012 | Farascioni et al. |
| 8,397,972 B2 * | 3/2013 | Kostrzewski ............... 227/175.2 |
| 2005/0070758 A1 | 3/2005 | Wells et al. |
| 2005/0139636 A1 | 6/2005 | Schwemberger et al. |
| 2005/0145672 A1 | 7/2005 | Schwemberger et al. |
| 2005/0184124 A1 | 8/2005 | Scirica et al. |
| 2005/0247752 A1 | 11/2005 | Kelly et al. |
| 2005/0247753 A1 | 11/2005 | Kelly et al. |
| 2006/0144898 A1 | 7/2006 | Bilotti et al. |
| 2006/0226195 A1 | 10/2006 | Scirica et al. |
| 2007/0029364 A1 | 2/2007 | Kruszynski et al. |
| 2007/0039995 A1 | 2/2007 | Schwemberger et al. |
| 2007/0039996 A1 | 2/2007 | Mather et al. |
| 2007/0039997 A1 | 2/2007 | Mather et al. |
| 2007/0114261 A1 | 5/2007 | Ortiz et al. |
| 2007/0175950 A1 | 8/2007 | Shelton, IV et al. |
| 2007/0181631 A1 | 8/2007 | Bilotti et al. |
| 2007/0219563 A1 | 9/2007 | Voegele |
| 2007/0221702 A1 | 9/2007 | Kruszynski |
| 2007/0246508 A1 | 10/2007 | Green |
| 2007/0255296 A1 | 11/2007 | Sauer |
| 2008/0027466 A1 | 1/2008 | Vitali et al. |
| 2008/0093415 A1 | 4/2008 | Bilotti |
| 2008/0169328 A1 | 7/2008 | Shelton |
| 2008/0169329 A1 | 7/2008 | Shelton et al. |
| 2008/0169330 A1 | 7/2008 | Shelton et al. |

(56) References Cited

U.S. PATENT DOCUMENTS

| | | |
|---|---|---|
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0272171 A1 | 11/2008 | Viola |
| 2008/0302854 A1 | 12/2008 | Rethy et al. |
| 2009/0008424 A1 | 1/2009 | Green |
| 2009/0134199 A1 | 5/2009 | Heinrich et al. |
| 2009/0206131 A1 | 8/2009 | Weisenburgh, II et al. |
| 2009/0272784 A1 | 11/2009 | Farascioni |
| 2010/0072258 A1 | 3/2010 | Farascioni et al. |

FOREIGN PATENT DOCUMENTS

| | | |
|---|---|---|
| EP | 0484677 | 5/1992 |
| EP | 0537498 | 4/1993 |
| EP | 0589306 | 3/1994 |
| EP | 0591946 | 4/1994 |
| EP | 0592243 | 4/1994 |
| EP | 0621009 | 10/1994 |
| EP | 0656188 | 6/1995 |
| EP | 1550410 | 7/2005 |
| EP | 1908413 | 4/2008 |
| FR | 2681775 | 10/1991 |
| WO | WO 03/022133 | 3/2003 |

* cited by examiner

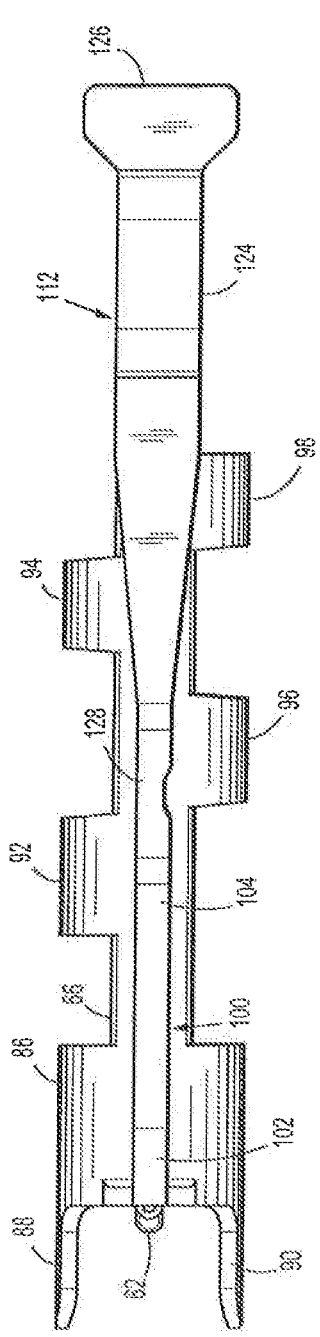
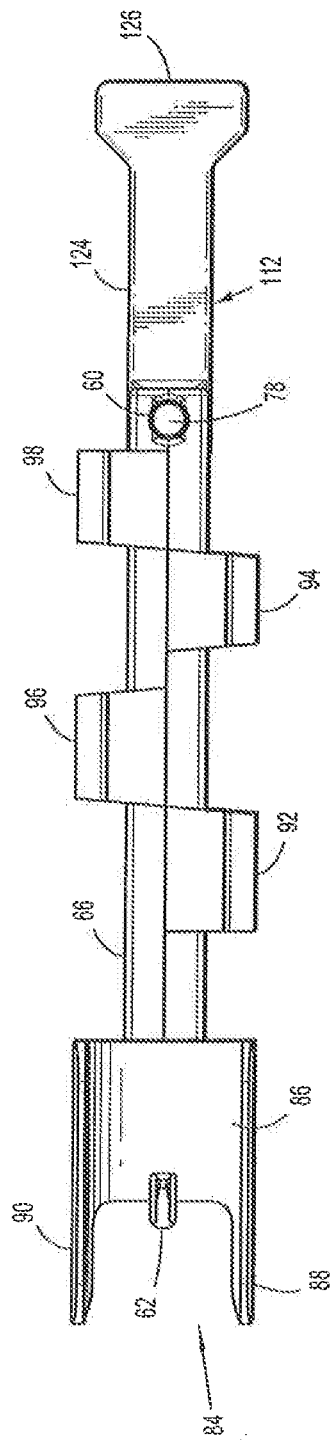

SHIPPING WEDGE WITH LOCKOUT

CROSS-REFERENCE TO RELATED APPLICATION

The present application is a continuation of U.S. patent application Ser. No. 13/051,276, filed on Mar. 18, 2011, now U.S. Pat. No. 8,397,972, the entire contents of which are incorporated herein by reference.

BACKGROUND

1. Technical Field

The present disclosure relates to a shipping safety device for use with a surgical instrument. More particularly, the present disclosure relates to a shipping wedge having a lockout member and a single use loading unit or "SULU" having a lockout mechanism for use with the surgical instrument.

2. Background of Related Art

In an effort to reduce trauma and recovery time, many surgical procedures are performed through small openings in the skin, such as an incision or a natural body orifice. Generally, such procedures are referred to as "endoscopic," unless performed on the patient's abdomen, in which case the procedure is referred to as "laparoscopic." Throughout the present disclosure, the term "minimally invasive" should be understood to encompass both endoscopic and laparoscopic procedures.

During the course of minimally invasive surgical procedures, a surgical fastener applying apparatus is often employed to connect adjacent sections of tissue. Many varieties of such apparatus are known in the art, some of which are specifically adapted for use in particular surgical procedures including, but not limited to, end-to-end anastomosis, circular end-to-end anastomosis, open gastrointestinal anastomosis, endoscopic gastrointestinal anastomosis, and transverse anastomosis. Examples of suitable surgical fastener applying apparatus are disclosed in U.S. Pat. Nos. 5,915,616; 6,202,914; 5,865,361; and 5,964,394. Typically, these surgical fastener applying apparatus include a first member that is movable relative to a second member such that target tissue is positionable therebetween to facilitate grasping and/or clamping of the target tissue.

Linear surgical fastener applying apparatus generally include two elongated jaw members, one of which includes a surgical fastener cartridge housing a plurality of surgical fasteners that are arranged in two or more linear rows, and the other of which includes an anvil component with a plurality of fastener forming pockets that are configured and dimensioned to receive and form the surgical fasteners upon ejection of the fasteners from the surgical fastener cartridge. The surgical fastener applying apparatus may also include a knife that is movable between the linear rows of surgical fasteners such that the tissue being joined and/or sealed is simultaneously, or sequentially, cut upon actuation of the surgical fastener applying apparatus. Given this capability, surgical fastener applying apparatus of the linear variety are commonly used during surgical procedures to simultaneously seal and cut target tissue, e.g., a patient's vasculature, organs, or the like.

Some surgical fastener applying apparatus are provided in two parts, a reusable handle or actuator section and a removable or replaceable single use loading unit or "SULU". The SULU includes the staple containing cartridge, anvil and a knife blade for cutting stapled tissue.

Safety devices may be provided to prevent movement of the knife blade during shipment and/or prior to use. In some instances, the safety devices can be removed from the SULU prior to the SULU being assembled to the reusable handle. Therefore, there exists a need for a shipping safety device and SULU having locking structure which prevents removal of the shipping safety device from the SULU prior to assembly with a reusable handle.

SUMMARY

In accordance with an embodiment of the present disclosure, there is provided a shipping wedge for use with a surgical instrument having a body portion. The shipping wedge includes a base configured to be detachably secured with the body portion of the surgical instrument, a blocking member depending from the base and engageable with a movable operative member of the surgical instrument, and a locking member depending from the base and engageable with a lockout mechanism of the surgical instrument.

In an embodiment, the blocking member may be a hook configured to engage with a knife member of the surgical instrument to inhibit movement of the knife member. The blocking member may be pivotably associated with the body portion. The base may include a proximal end portion including the locking member and a distal end portion including the blocking member. In particular, the blocking member may extend distally from the base.

In another embodiment, the locking member may include an enlarged flange. The flange may be a circular disc. The shipping wedge may include a downward extension connecting the circular disc to the base. The circular disc may have a diameter larger than a width of the downward extension.

In still another embodiment, the shipping wedge may further include flexible arms projecting from the base, wherein the flexible arms are shaped to cooperated with the body portion of the surgical instrument.

In accordance with another embodiment of the present disclosure, there is provided a surgical instrument including an elongate member, a loading unit detachably coupled to the elongate member, and a removable safety device. The loading unit includes a body portion, a movable operative device disposed in the body portion, and a lockout mechanism including a locking plate movably mounted to the body portion. The locking plate is movable between a locked position and an unlocked position. The removable safety device includes a blocking member engageable with the movable operative device and a lockout member engageable with the locking plate, wherein the removable safety device is locked to the body portion of the loading unit when the locking plate is in the locked position and is unlocked for removal from the body portion when the locking plate is in the unlocked position.

In an embodiment, the lockout member may include a neck portion and a flange portion extending from the neck portion. The locking plate may include a keyhole slot including a first portion configured to receive the flange portion of the lockout member and a second portion configured to receive the neck portion. The flange portion may be a circular disc.

In yet another embodiment, the loading unit may further include a biasing member configured to bias the locking plate toward the locked position.

In still yet another embodiment, the movable operative device may be a knife member.

In still yet another embodiment, the loading unit may further include an actuator configured to move the locking plate upon actuation of the actuator.

DESCRIPTION OF THE DRAWINGS

An embodiment of the presently disclosed shipping wedge with lockout is disclosed herein with reference to the drawings, wherein:

FIG. 5 is a top plan view of the shipping wedge;

FIG. 6 is a bottom plan view of the shipping wedge;

DETAILED DESCRIPTION OF EMBODIMENTS

An embodiment of the presently disclosed shipping wedge with lockout will now be described in detail with reference to the drawings wherein like numerals designate identical or corresponding elements in each of the several views. As is common in the art, the term 'proximal" refers to that part or component closer to the user or operator, i.e. surgeon or physician, while the term "distal" refers to that part or component further away from the user.

Figure 1:
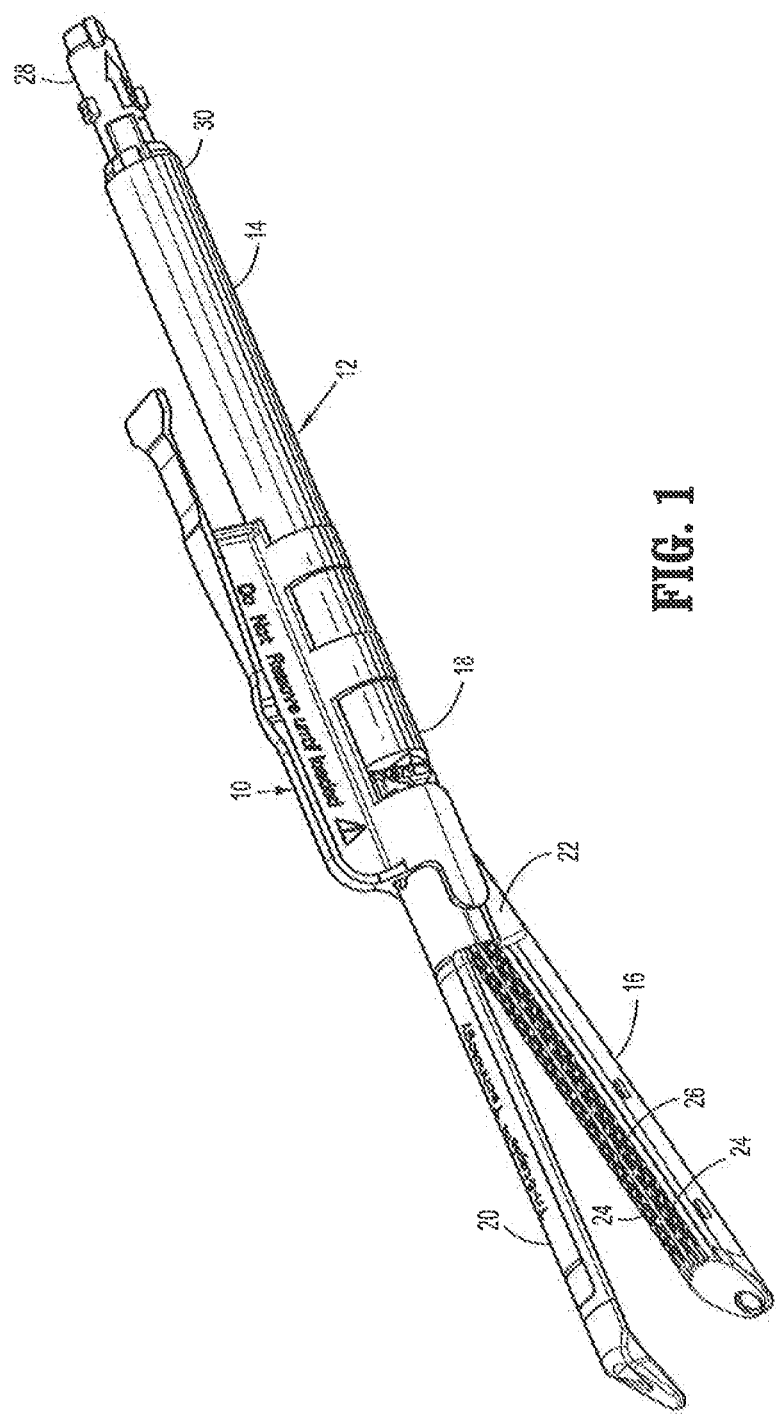
FIG. 1 is a perspective view of an embodiment of a shipping wedge with lockout ("shipping wedge") installed on a Single Use Loading Unit ("SULU")

Referring initially to FIG. 1, there is disclosed a surgical stapling instrument 10 according to an embodiment of the present disclosure. The instrument has a Loading Unit 12, e.g. a "SULU", and a shipping wedge or loading lock 10. The loading unit 12 is provided as a self contained, replacable device which is removably attachable to the surgical stapling instrument in order to allow for multiple uses of the surgical stapling instrument. Loading unit 12 generally includes an elongate tubular member 14 having a staple cartridge 16 mounted to a distal end 18 of elongate tubular member 14. An anvil member 20 extends from and is affixed to distal end 18 of elongate tubular member 14. Staple cartridge 16 is movable from an open position spaced from anvil member 20 to a closed position in close cooperative alignment with anvil member 20 to clamp tissue therebetween. Specifically, a proximal end 22 of staple cartridge 16 is movably mounted to distal end 18 of elongate tubular member 14. Staple cartridge 16 is movable between the open and closed position in response to operation of an actuator (not shown) associated with the surgical stapling instrument.

Staple cartridge 16 includes pluralities of rows of staple containing pockets 24. Staples (not shown) contained in rows of staple containing pockets 24 are ejected out of staple cartridge 16, through tissue, and crimped against anvil member 20 in response to operation of an actuator such as a movable handle trigger. In order to accommodate a knife blade to sever the stapled tissue, staple cartridge 16 includes a longitudinal knife slot 26 extending between plurality of rows of staple containing pockets 24. Knife slot 26 allows for passage of the knife blade (see FIGS. 21 and 22) through the stapled tissue. When installed on loading unit 12, shipping wedge 10 prevents movement of the knife blade through knife slot 26 in a manner described hereinbelow.

A connector assembly 28 extends from a proximal end 30 of elongate tubular member 14 and is provided to allow loading unit 12 to be operatively connected to the surgical stapling instrument.

Figure 2:
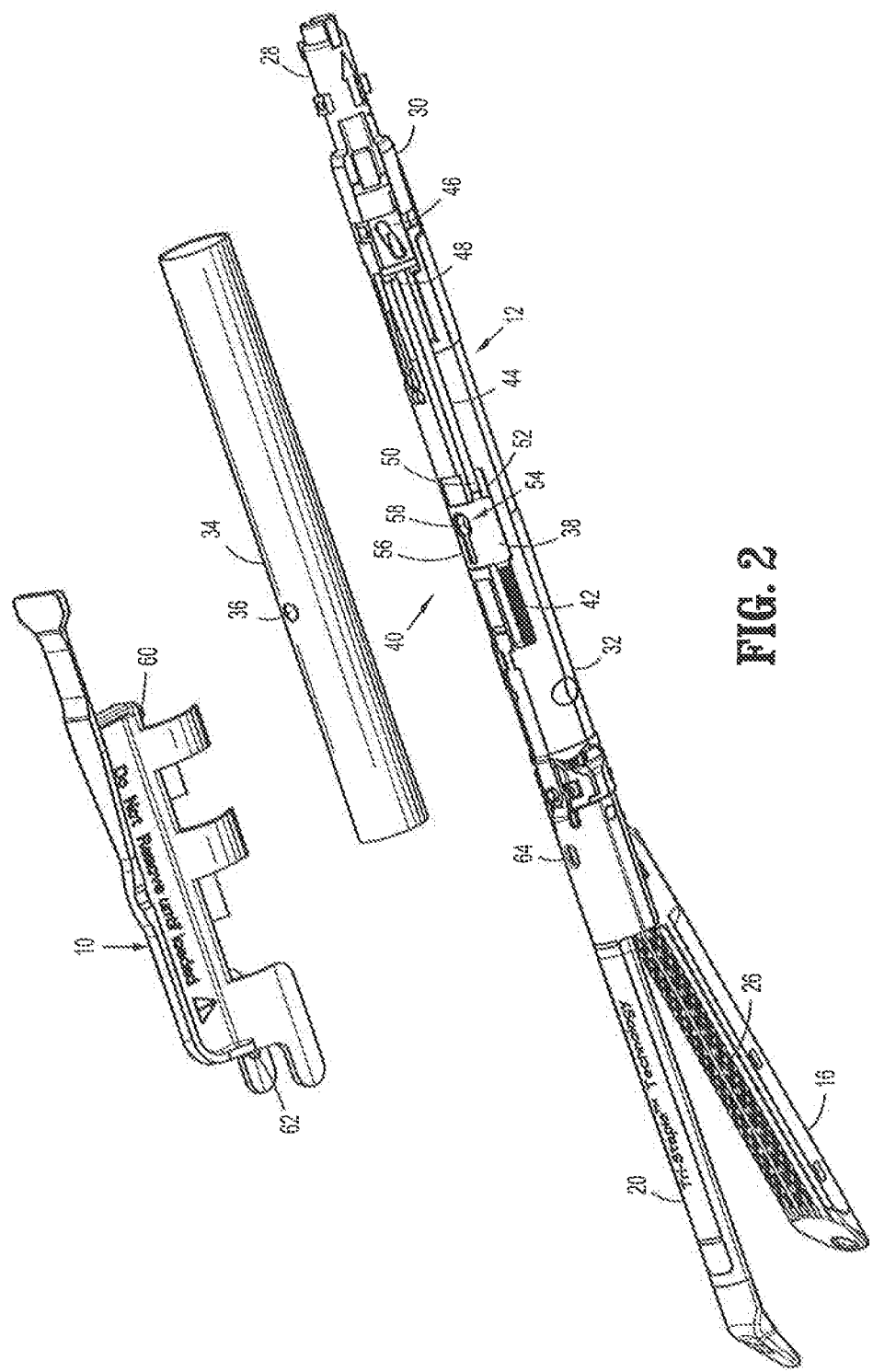
FIG. 2 is a perspective view of the shipping wedge and SULU with parts separated.
Figure 3:
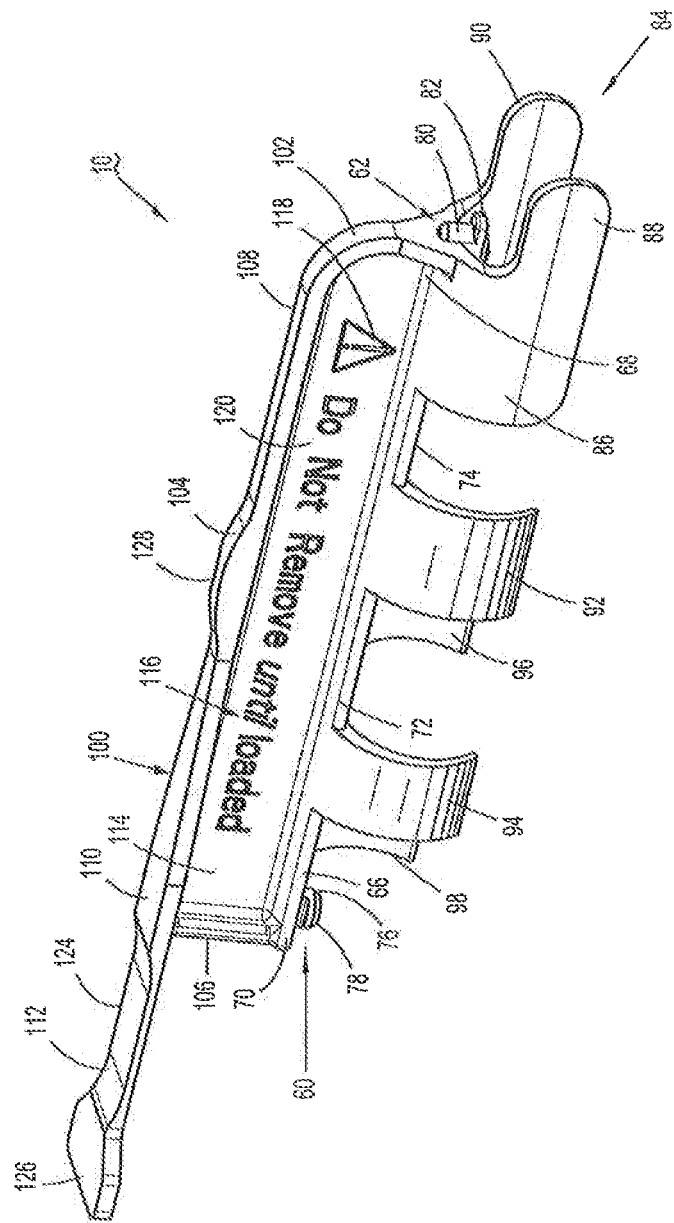
FIG. 3 is a perspective view of the shipping wedge.
Figure 4:
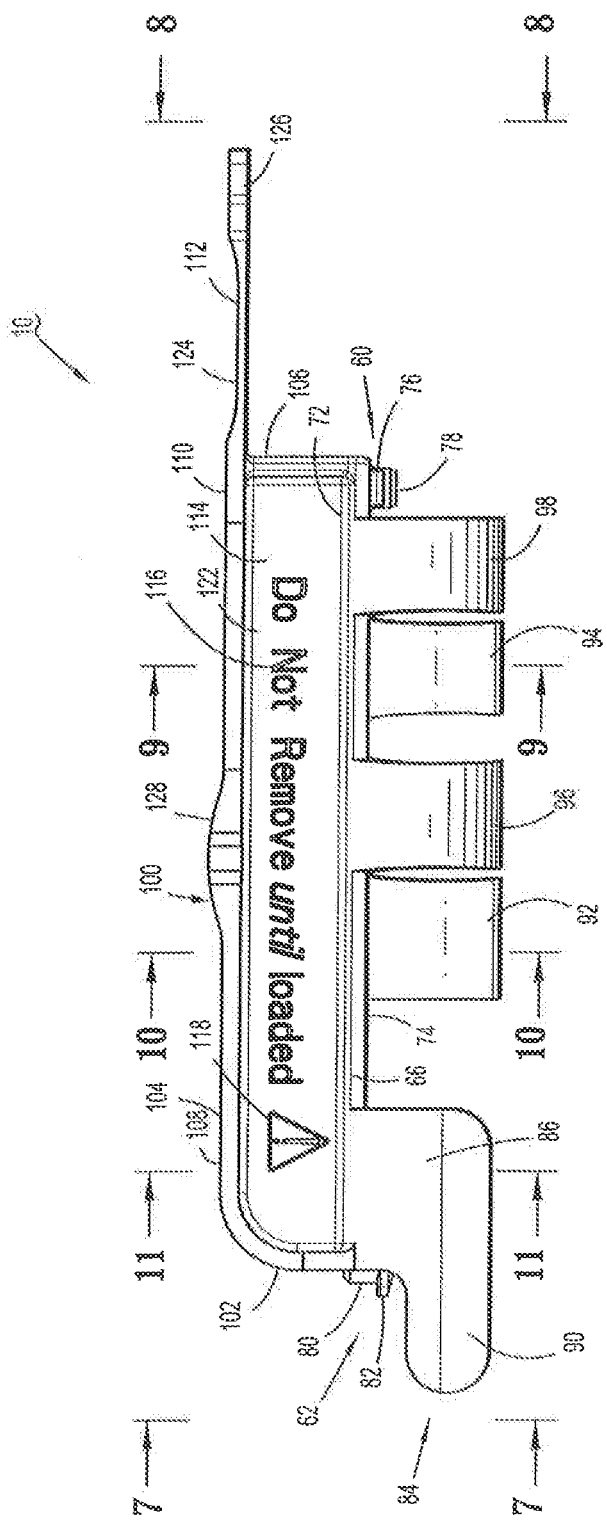
FIG. 4 is a side plan view of the shipping wedge.

Referring now to FIG. 2, loading unit 12 includes a body portion 32 having a cover tube 34 overlying body portion 32. A hole 36 is provided through cover tube 34 and functions with a locking plate 38, movably mounted on body portion 32, to form part of a locking mechanism 40 which prevents removal of shipping wedge 10 from elongate tubular member 14 prior to installation of loading unit 12 on a surgical stapling instrument. Locking mechanism 40 additionally includes a biasing or compression spring 42 to bias locking plate 38 proximally relative to body portion 32. An extension rod 44 abuts locking plate 38 and extends along body portion 32 from an actuator 46 on body portion 32. Specifically, a proximal end 48 of extension rod 44 engages actuator 46 while a distal end 50 of extension rod 44 engages a proximal edge 52 of locking plate 38. Movement of actuator 46 distally drives extension rod 44 and locking plate 38 distally along body portion 32 against the bias of compression spring 42.

Locking plate 38 includes a key hole slot 54 having a distal longitudinal keyway 56 and a proximal hole 58. Shipping wedge 10 includes a proximal locking pin 60 which is insertable through hole 36 in cover tube 34 and into key hole slot 54 in locking plate 38. Engagement of key way 56 of locking plate 38 with proximal locking pin 60 secures shipping wedge 10 against loading unit 12 until loading unit 12 has been properly installed into a surgical stapling instrument or until actuator 46 has been manually moved in a manner described in more detail hereinbelow. Shipping wedge or loading lock 10 additionally includes a distal hook 62 which is insertable through a hole 64 formed through distal end 18 of elongate tubular member 14 and serves to block movement of a knife 17 (see FIG. 17) through knife slot 26 in staple cartridge 16 when shipping wedge 10 is installed on loading unit 12.

Referring now to FIGS. 3-11, and initially with regard to FIGS. 3-6, the details of shipping wedge 10 will now be described. Shipping wedge 10 includes a generally elongate rectangular base 66 having a distal end 68, a proximal end 70, an upper surface 72 and a lower surface 74. Proximal locking pin 60 projects from lower surface 74 at proximal end 70 of base 66 while distal hook 62 projects from lower surface 74 at distal end 72 of base 66. With specific reference to FIGS. 3 and 4, proximal locking pin 60 includes a downward extension 76 extending from lower surface of 74 of base 66. Downward extension 76 terminates in an enlarged, circular locking flange 78. Distal hook 62 also has a downward extension 80 which terminates in a distally projecting lip 82. Locking flange 78 is positionable through hole 36 in cover tube 34 and hole 58 in key hole slot 54 of locking plate 38 while distally projecting lip 82 is insertable into hole 64 in elongate tubular member 14 (see also FIG. 2).

In order to initially position distal hook 62 relative to hole 64 in elongate tubular member 14 (FIG. 2), shipping wedge 10 includes a distally projecting, semi-cylindrical alignment unit 84. Alignment unit 84 includes a semi-cylindrical proximal portion 86 and a pair of distally extending alignment arms 88 and 90 extending distally from proximal portion 86. Proximal portion 86 and alignment arms 88 and 90 are relatively flexible so as to engage elongate tubular member 14 in snap fit fashion.

Referring to FIGS. 3-6, in order to further secure shipping wedge 10 on elongate tubular member 14 in snap fit fashion, shipping wedge 10 includes flexible arms 92, 94, 96 and 98 projecting downwardly from base 66. The flexible arms are shaped to cooperate with the cover tube and body portion. Flexible arms 92, 94, 96 and 98 are arcuate in shape and spaced longitudinally along base 66. For example, flexible arcuate arms 92 and 94 are longitudinally spaced along one side of base 66 while flexible arcuate arms 96 and 98 are spaced distally along an opposed side of base 66. In addition, flexible arcuate arms 92 and 94 are staggered longitudinally relative to flexible arcuate arms 96 and 98.

Shipping wedge 10 additionally includes a grasping frame 100 to facilitate manipulation of shipping wedge 10 onto elongate tubular member 14. Grasping frame 100 generally includes an arcuate distal portion 102, a central portion 104 and a proximal portion 106. Distal portion 102 extends from a distal end 108 of central portion 104 to distal end 68 of base 66. Likewise, proximal portion 106 extends from a proximal end 110 of central portion 104 to proximal end 70 of base 66. A thumb tab 112 extends proximally from proximal end 110 of central portion 104 to facilitate removal of shipping wedge 10 from elongate tubular member 14 in a manner described in more detail hereinbelow. An indicia plate 114 is provided between base 66 and grasping frame 100 and serves to strengthen or stiffen shipping wedge 10 as well as provide space for text and symbol indicia 116 and 118, respectively, on opposed sides 120 and 122 of indicia plate 114. Thumb tab 112 of shipping wedge 10 includes a flexible arm 124 terminating in an enlarged end 126. A central raised rib 128 is provided on central portion 104 of grasping frame 100.

Figure 7:
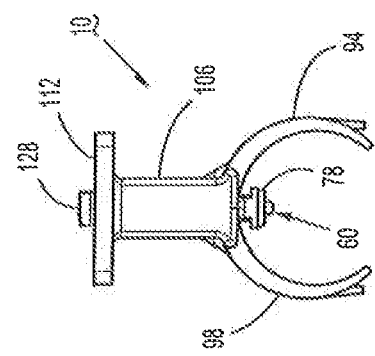
FIG. 7 is an end view taken along line 7-7 of FIG. 4.
Figure 8:
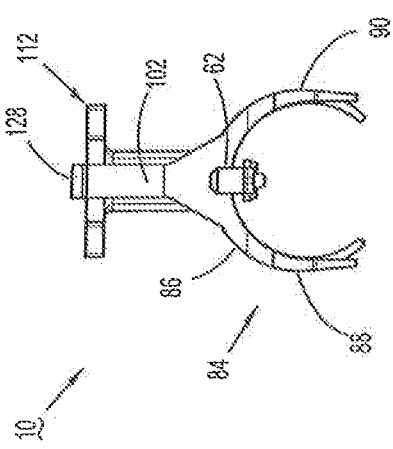
FIG. 8 is an opposite end view taken along line 8-8 of FIG. 4.

As best shown in FIG. 7, distal hook 62 projects downwardly through semicylindrical alignment unit 84 and between distally extending alignment arms 88 and 90. As best seen in FIG. 8, proximal locking pin 60, including circular locking flange 78, projects downwardly into the space defined by the flexible arcuate arms 94 and 98.

Shipping wedge 10 may be formed from a variety of relatively flexible materials such as, for example, polymeric materials, metallic materials, etc. Forming shipping wedge 10 from flexible materials allows alignment arms 88 and 90 of distally projecting alignment unit 84, as well as flexible arcuate arms 92, 94, 96 and 98, to flex outwardly around loading unit 12 to allow shipping wedge 10 to be attached to loading unit 12 in snap fit fashion. Similarly, the flexible nature of the materials forming shipping wedge 10 allows thumb tab 112 to flex slightly to facilitate removal of shipping wedge 10 from loading unit 12. As noted herein above, shipping wedge 10 includes base 66 which, in conjunction with grasping frame 100 and indicia plate 114, provides sufficient rigidity to shipping wedge 10 in order to prevent undue flexing and inadvertent dislodgement of shipping wedge 10 from loading unit 12.

Figure 11:
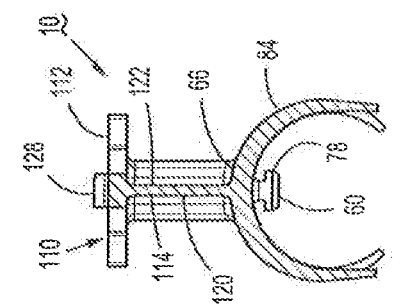
FIG. 11 is a cross-sectional view taken along line 11-11 of FIG. 4.
Figure 10:
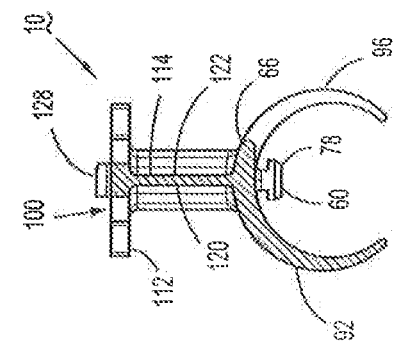
FIG. 10 is a cross-sectional view taken along line 10-10 of FIG. 4.
Figure 9:
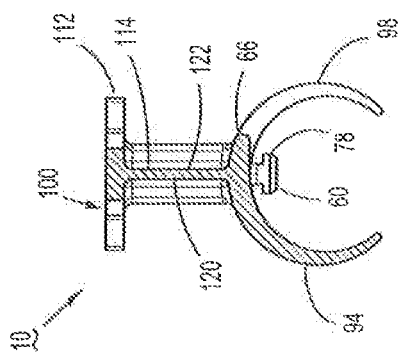
FIG. 9 is a cross-sectional view taken along line 9-9 of FIG. 4.

The elements of shipping wedge 10 may be formed from a variety of separate components which are then welded, glued or otherwise assembled or, with specific reference to FIGS. 9-11, shipping wedge 10 maybe formed integrally as one single, monolithic molded or machined unit. For example, as shown in FIG. 9, flexible arcuate arm 94 is illustrated integral with indicia plate 114 and grasping frame 100 while in FIG. 10, flexible arcuate arm 92 is illustrated integral with indicia plate 114 and grasping frame 100. As best shown in FIG. 11, distally projecting alignment unit 84 is illustrated as being formed integral with indicia plate 114 and grasping frame 110.

Figure 12:
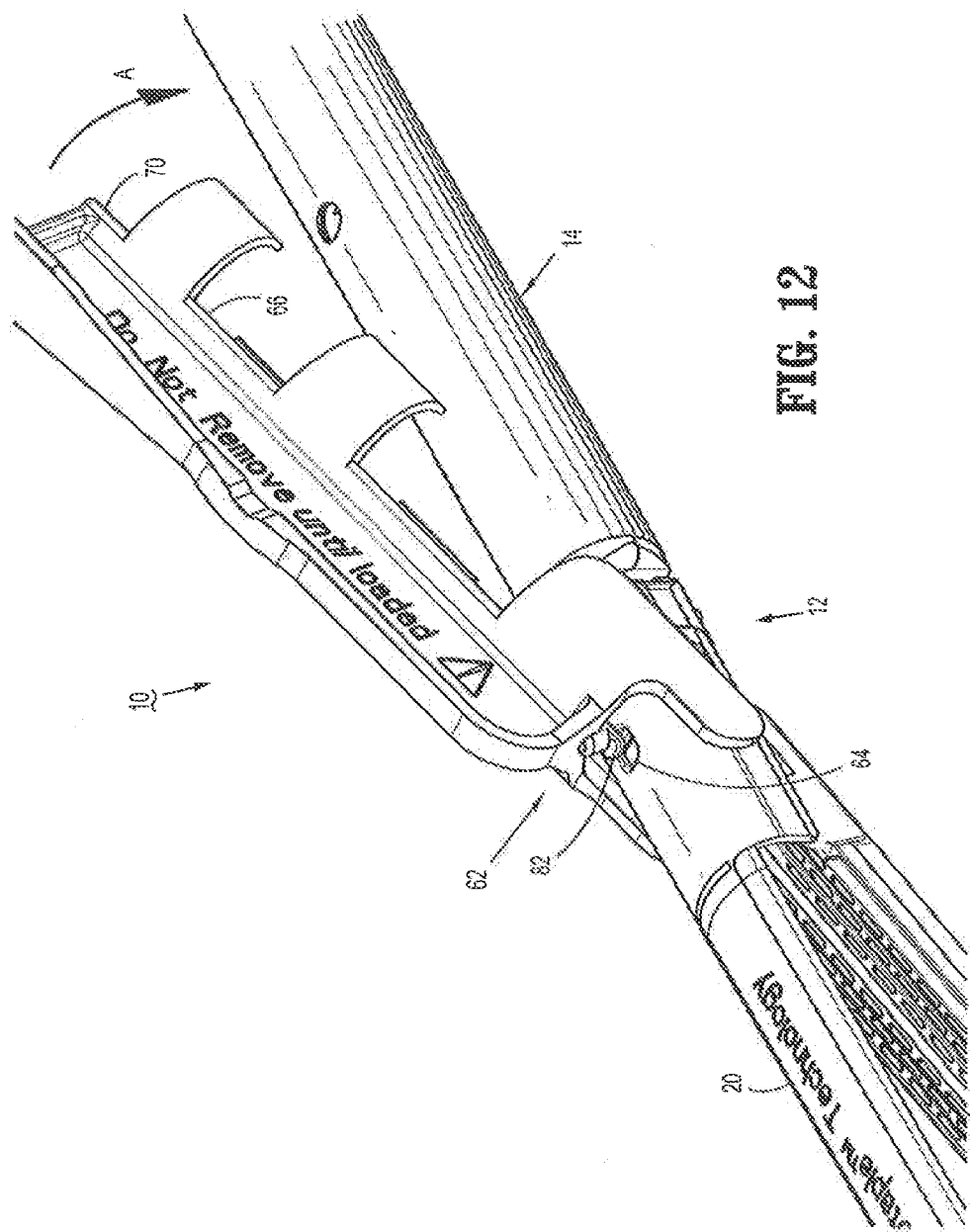
FIG. 12 is a perspective view illustrating a distal end of the shipping wedge during initial installation into the SULU.
Figure 13:
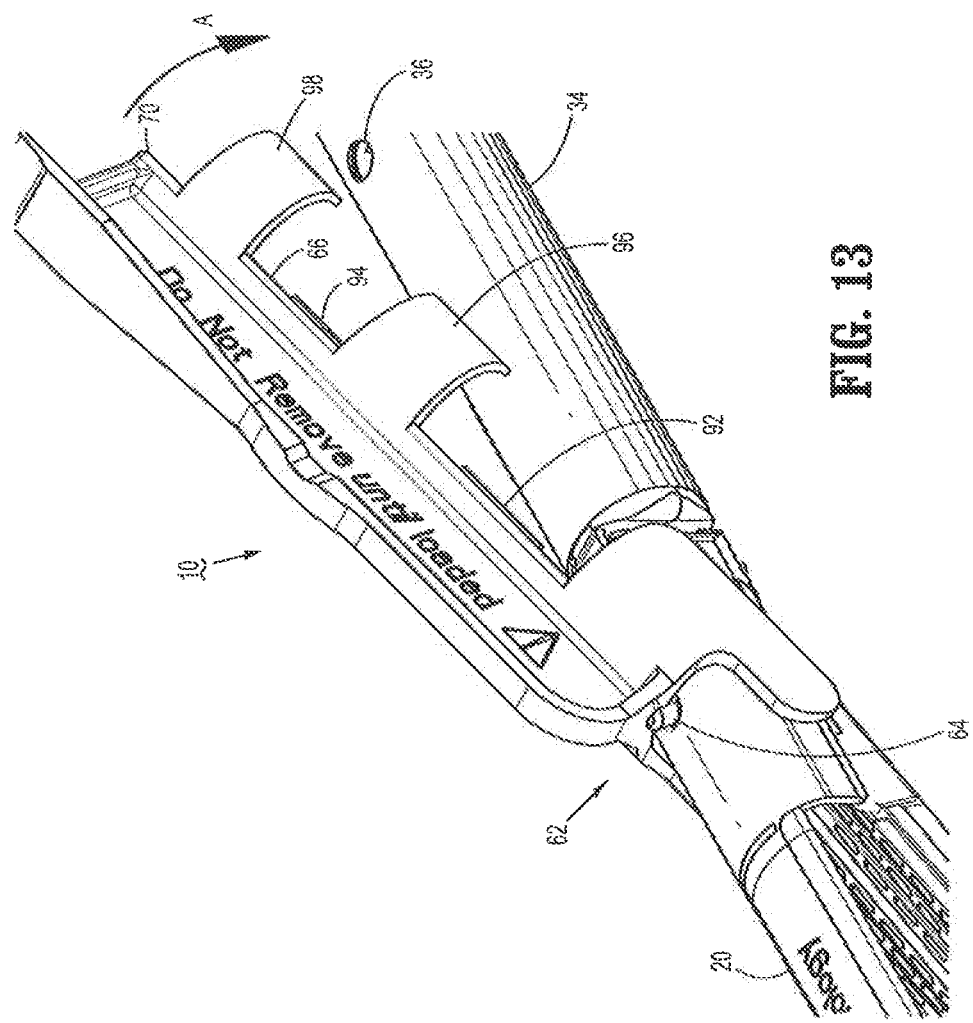
FIG. 13 a perspective view similar to FIG. 12 illustrating further installation of the shipping wedge into the SULU.
Figure 14:
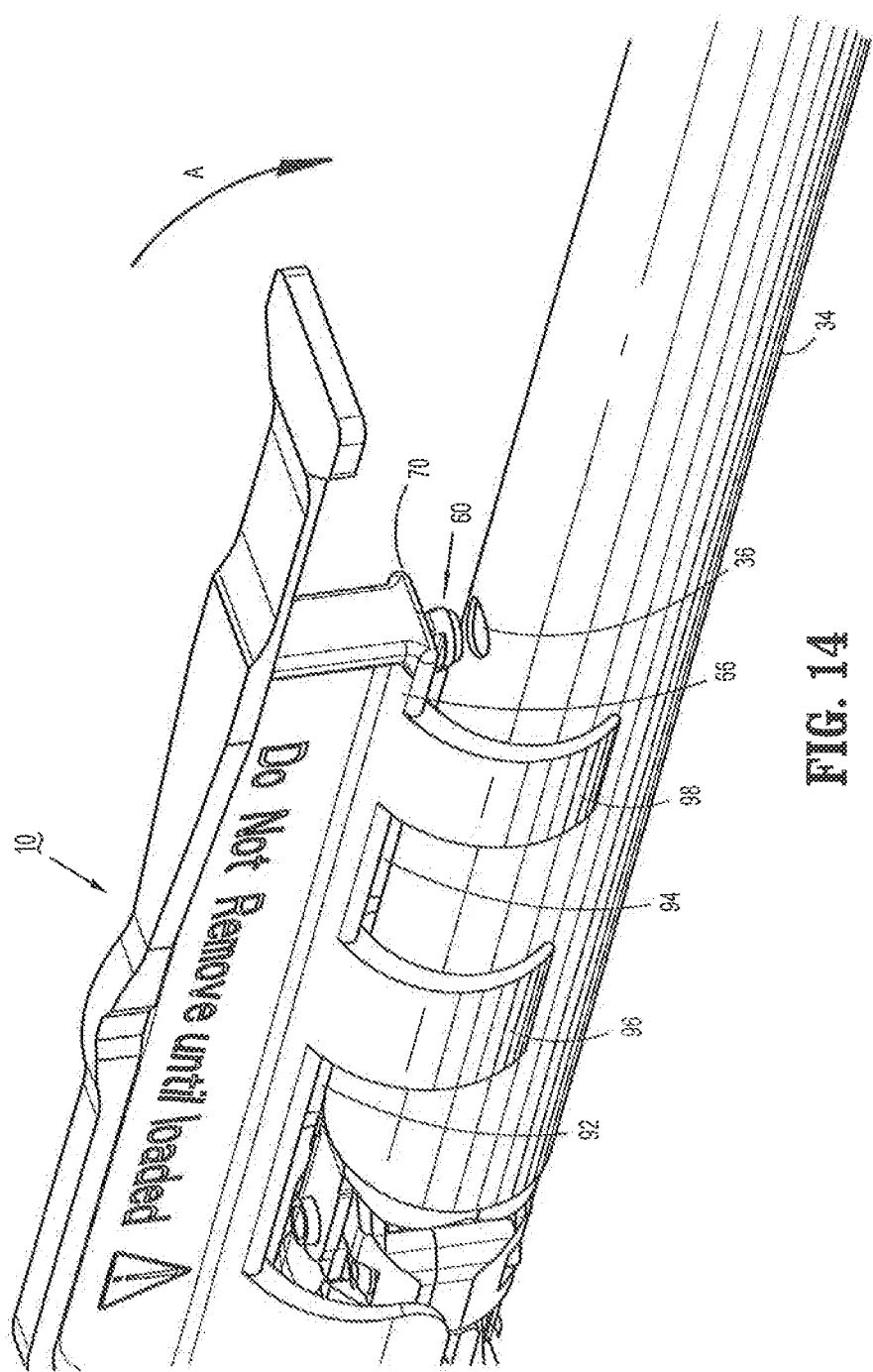
FIG. 14 is a perspective view of a proximal end of the shipping wedge positioned adjacent the SULU.

Referring now to FIGS. 2, 3 and 12-22, the use of shipping wedge 10 in conjunction with lockout mechanism 40 on loading unit 12 will now be described. Referring initially to FIGS. 12 and 13, in order to assemble shipping wedge 10 to loading unit 12, shipping wedge 10 is initially positioned adjacent loading unit 12 such that alignment arms 88 and 90 surround anvil 20 and distal hook 62 of shipping wedge 10 is positioned over hole 64 in anvil 20. Shipping wedge or loading lock 10 is then manipulated such that distally projecting lip 82 of distal hook 62 enters hole 64 (FIG. 13). Thereafter, with reference to FIGS. 12-14, proximal end 70 of base 66 is pivoted downwardly in the direction of arrow A, causing flexible arcuate arms 92, 94, 96 and 98 to engage and flex around cover tube 34 of loading unit 12. As noted herein above, flexible arcuate arms 92, 94, 96 and 98 are provided to secure shipping wedge 10 against loading unit 12 and prevent shipping wedge 10 from inadvertently falling off loading unit 12. With specific reference to FIG. 14, in this condition, proximal locking pin 60 of shipping wedge 10 is positioned adjacent hole 36 in cover tube 34.

Figure 15:
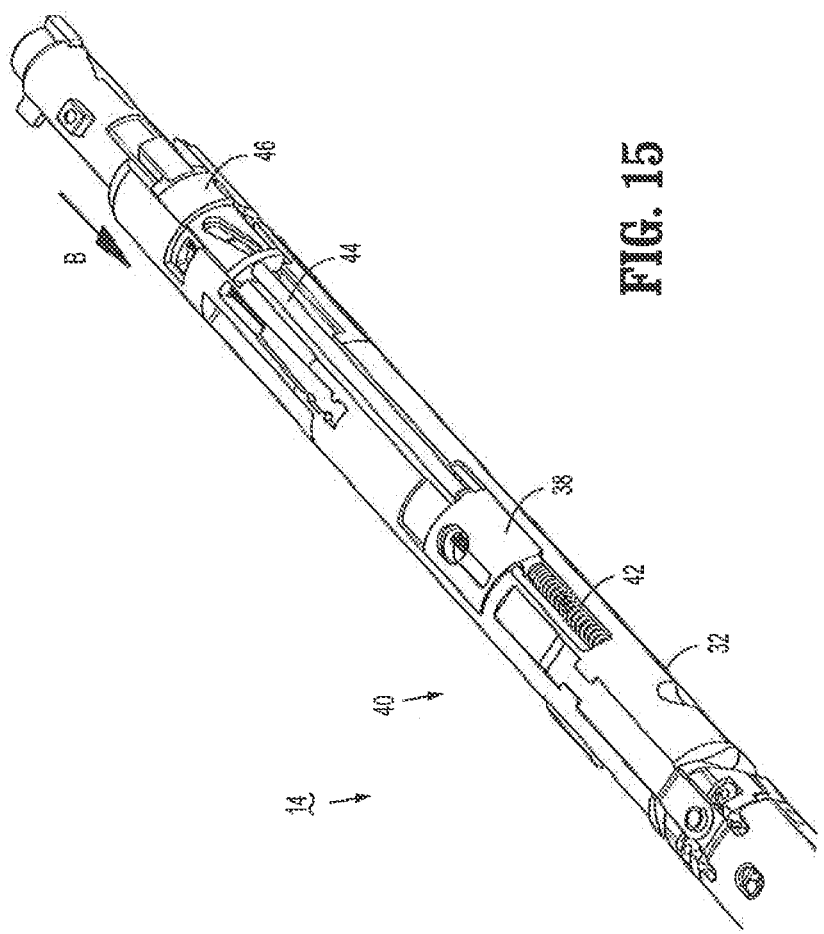
FIG. 15 is a perspective view of the SULU with a cover tube removed.
Figure 16:
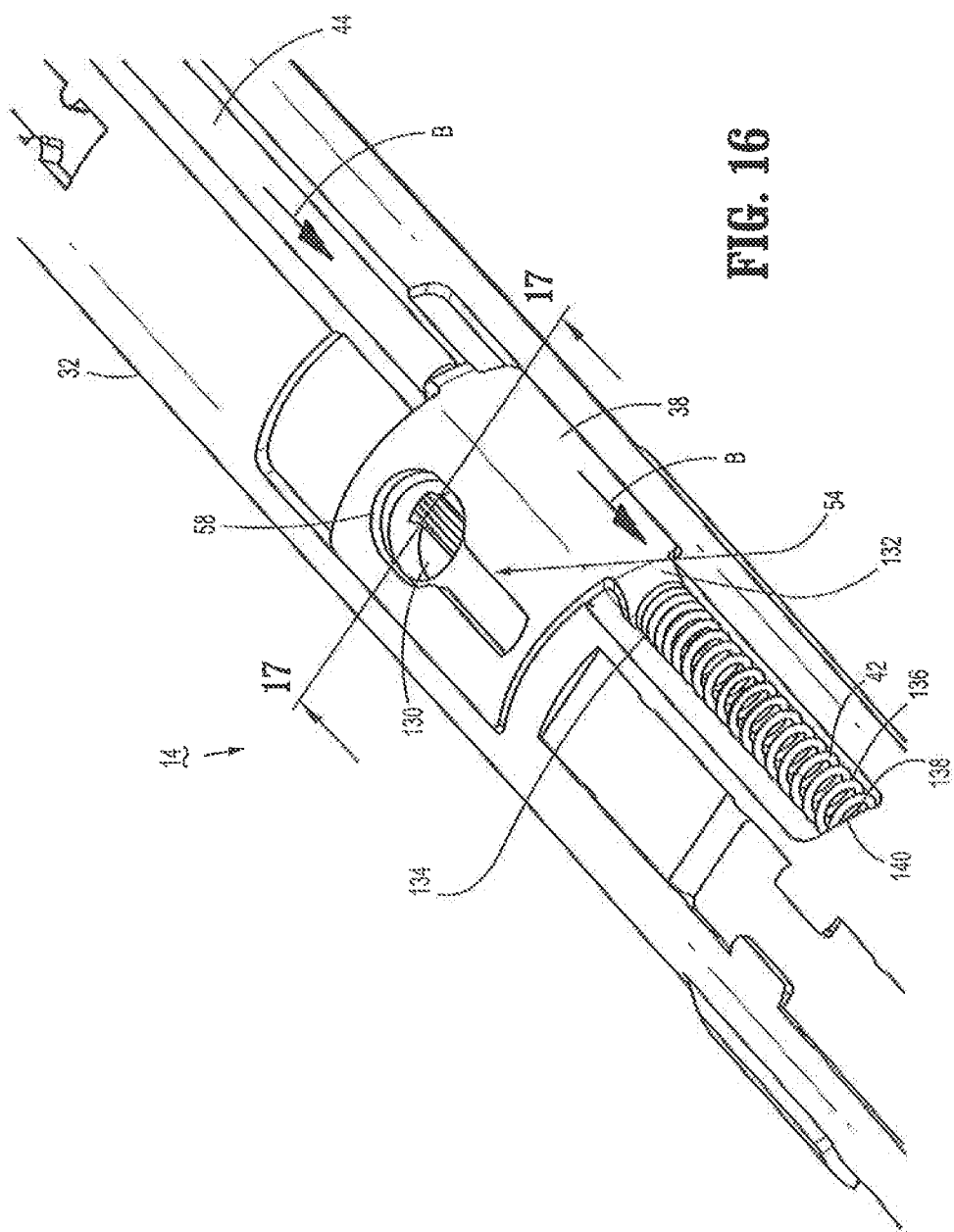
FIG. 16 is an enlarged perspective view of the SULU illustrating a locking mechanism in an unlocked position on the SULU.

Referring to FIGS. 15 and 16, during the initial or factory installation of shipping wedge 10 to loading unit 14, locking mechanism 40 is artificially manipulated into an unlocked condition by advancing actuator 46 distally in the direction of arrow B. Movement of actuator 46 distally drives extension rod 44 and locking plate 38 distally relative to body portion 32 of elongate tubular member 14 and against the bias of compression spring 42. As specifically shown in FIG. 16, when locking plate 38 is in the distal most position relative to body portion 32 of elongate tubular member 14, hole 58 of key hole slot 54 in locking plate 38 is positioned directly above a depression 130 formed in body portion 32 of elongate tubular member 14. As further best shown in FIG. 16, locking plate 38 includes a distal arm 132 which engages a proximal end 134 of compression spring 42. Compression spring 42 is constrained within a spring trough 136 formed in body portion 32. A distal end 138 of compression spring 42 abuts a distal end 140 of spring trough 136.

Figure 17:
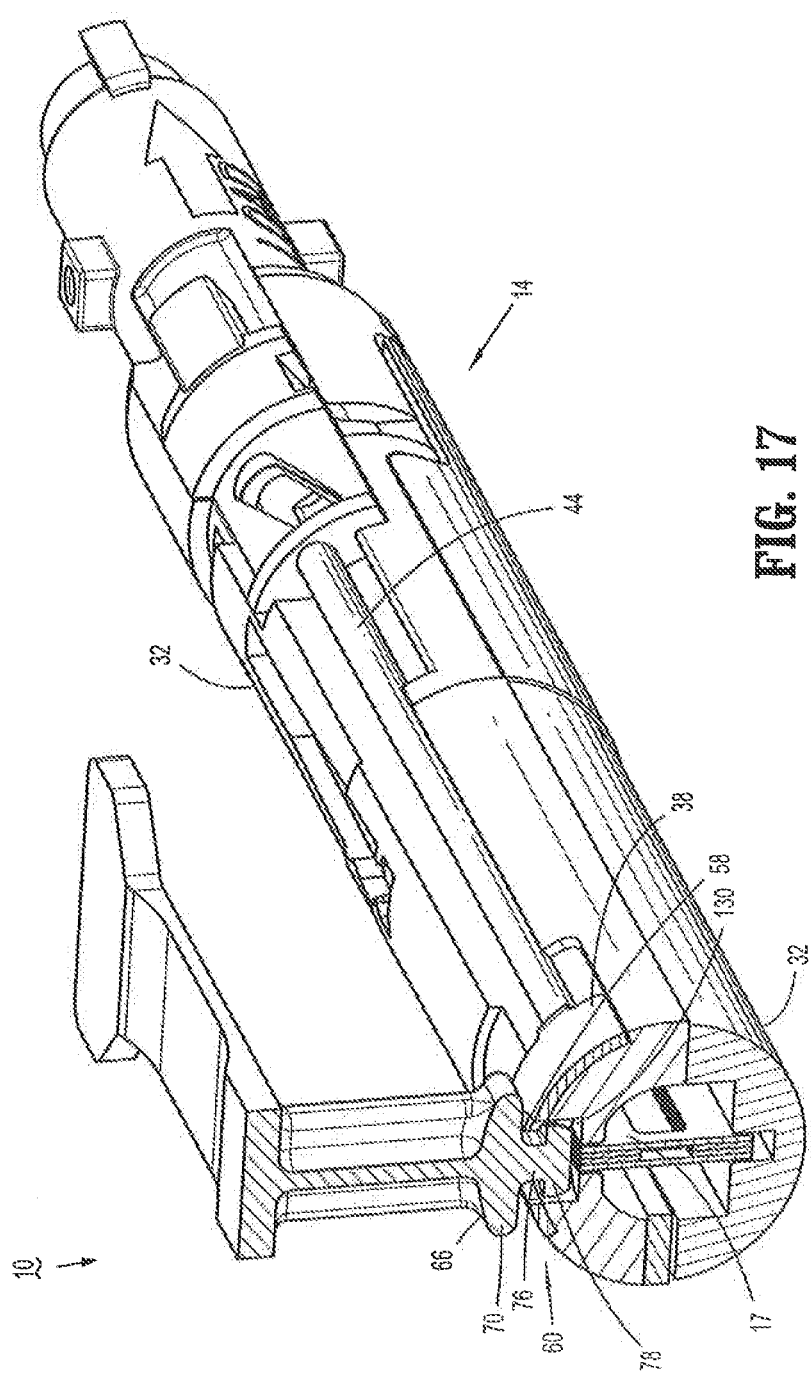
FIG. 17 is a cross-sectional view taken along line 17-17 of FIG. 16 with the shipping wedge installed through the locking mechanism.

With specific reference now to FIG. 17, once shipping wedge 10 has been fully manipulated in the direction of the arrow A to bring flexible arcuate arms 92, 94, 96 and 98 into engagement with cover tube 34 (FIG. 14), proximal locking pin 60 of shipping wedge 10 is seated in depression 130 in body portion 32 of elongate tubular member 14 such that circular locking flange 78 of proximal locking pin 60 is within depression 130 and downward extension 76 of proximal locking pin 60 is positioned within hole 58 of key hole slot 54 in locking plate 38. In this position, locking plate 38 is in the distal most or unlocked condition enabling proximal locking pin 60 of shipping wedge 10 to be inserted and subsequently removed through keyhole slot 54 of locking plate 38.

Figure 18:
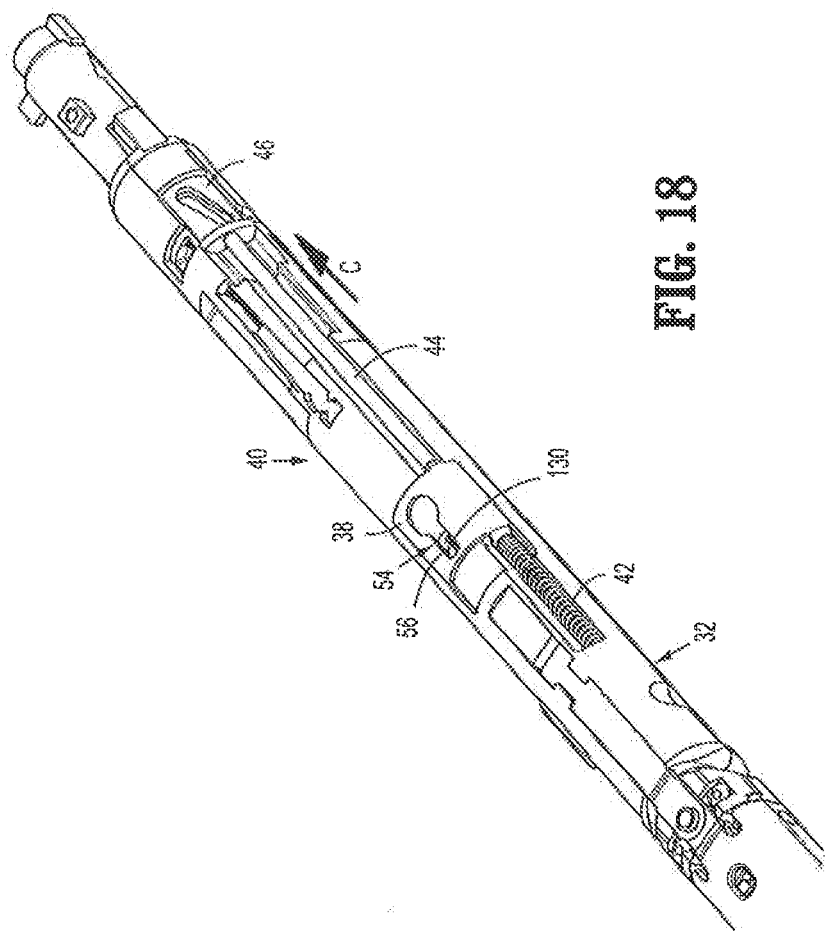
FIG. 18 is a perspective view similar to FIG. 15 with the locking mechanism in a locked position.
Figure 19:
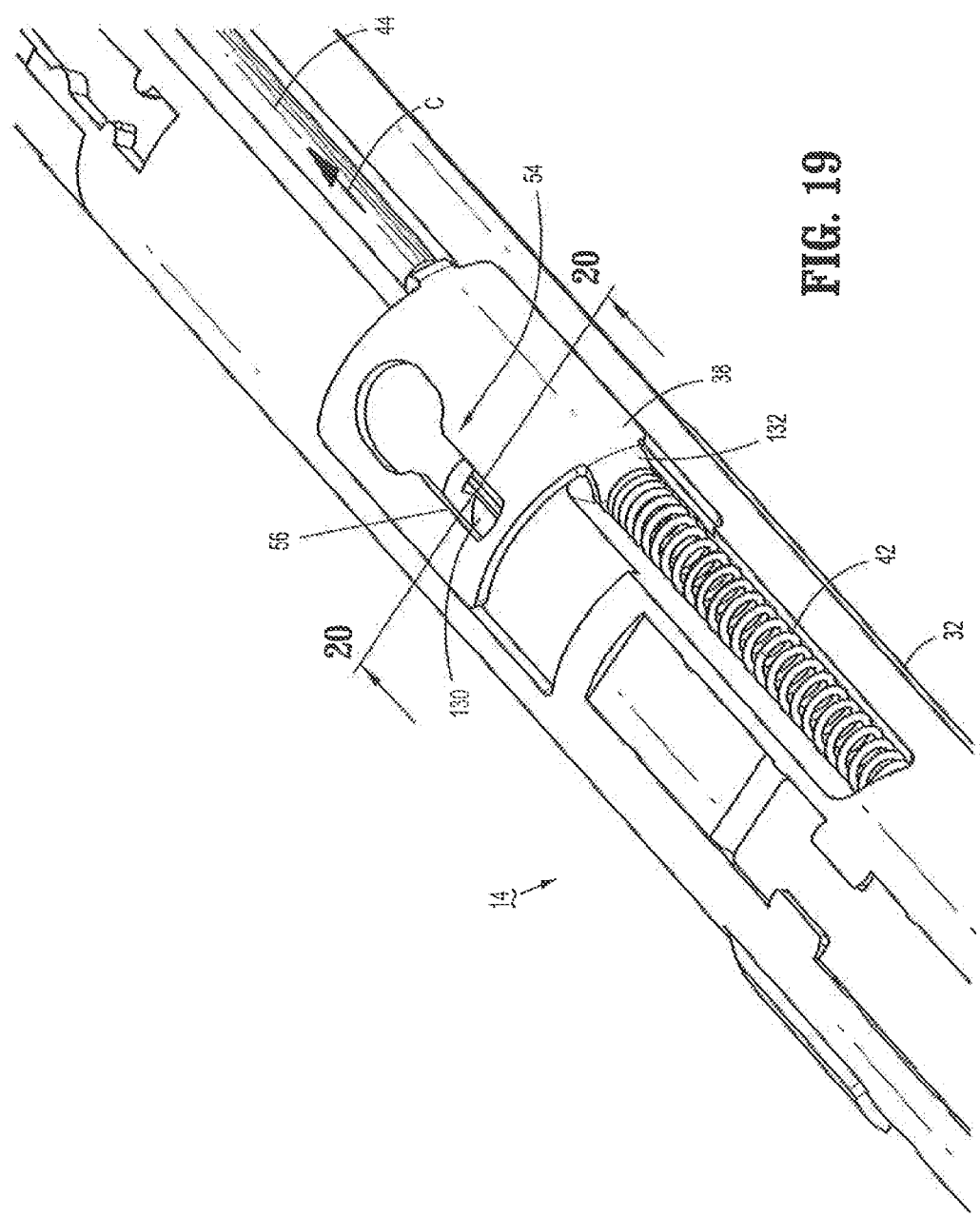
FIG. 19 is an enlarged perspective view similar to FIG. 16 with the locking mechanism in the locked position.

Referring now to FIGS. 18 and 19, in order to move locking plate 38 into a locked condition distal pressure is removed from actuator 46 allowing lockout mechanism 40, including extension rod 44 and lockout plate 38 to move proximally in the direction of arrow C against the bias of compression spring 42. As specifically shown in FIG. 19, when locking plate 38 is in a proximal most position, narrower width keyway 56 of keyhole slot 54 is located over depression 130 formed a body portion 32 of elongate tubular member 14.

Figure 20:
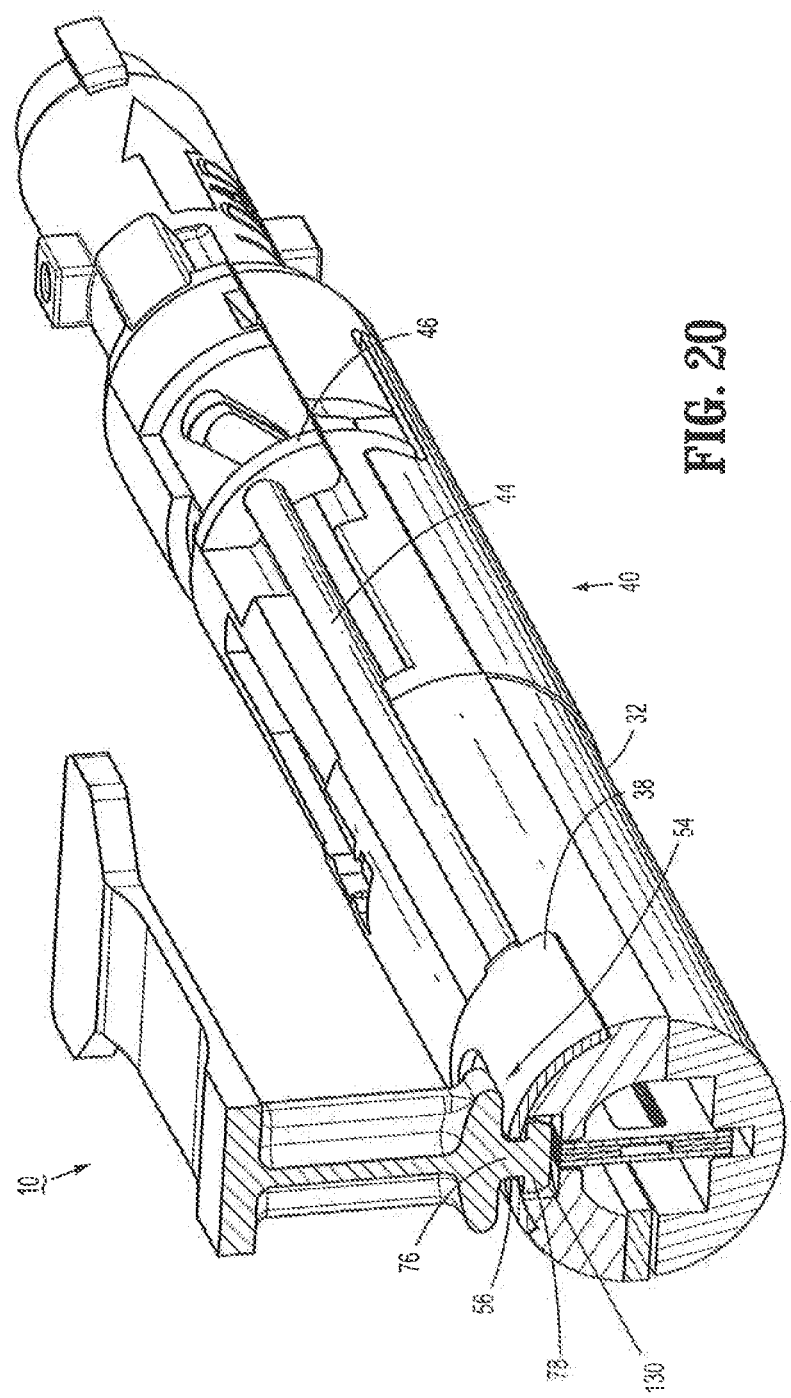
FIG. 20 is a cross-sectional view taken along line 20-20 of FIG. 19 with the shipping wedge in the locked condition.

With reference to FIG. 20, it can be seen that with locking plate 38 of lockout mechanism 40 in a proximal or a locked position, downward extension 76 of proximal locking pin 60 is positioned within keyway 56 of keyhole slot 54. Circular locking flange 78 of proximal locking pin 60, being larger in diameter than the width of keyway 56 in keyhole slot 54, prevents removal of proximal locking pin 60 out of depression 130 formed in body portion 32. This prevents shipping wedge 10 from being removed from body portion 32 and, in turn, loading unit 14 when locking mechanism 40, and specifically locking plate 38, is in the distal most or locked condition. In this manner, locking mechanism 40 completely prevents removal of shipping wedge 10 from loading unit 12 until such time as locking mechanism 40 has been moved to the unlocked condition either artificially during initial assembly of shipping wedge 10 to loading unit 12 or, more importantly, during movement of actuator 46 distally by installation of loading unit 12 fully into a surgical stapling instrument.

Figure 21:
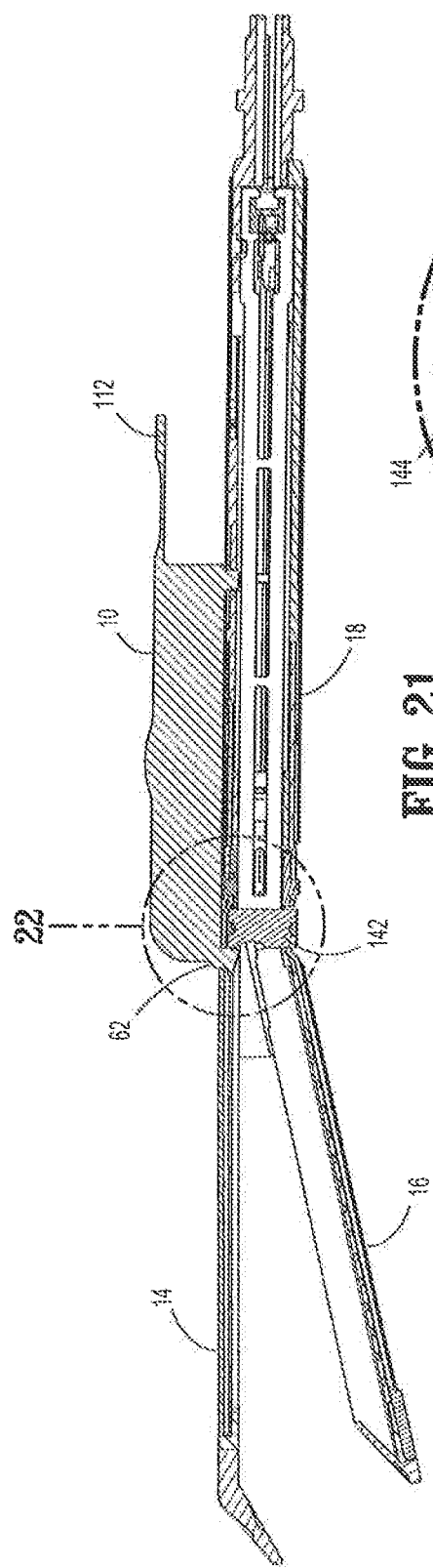
FIG. 21 is a cross-sectional view of the shipping wedge installed on the SULU and in the locked condition.
Figure 22:
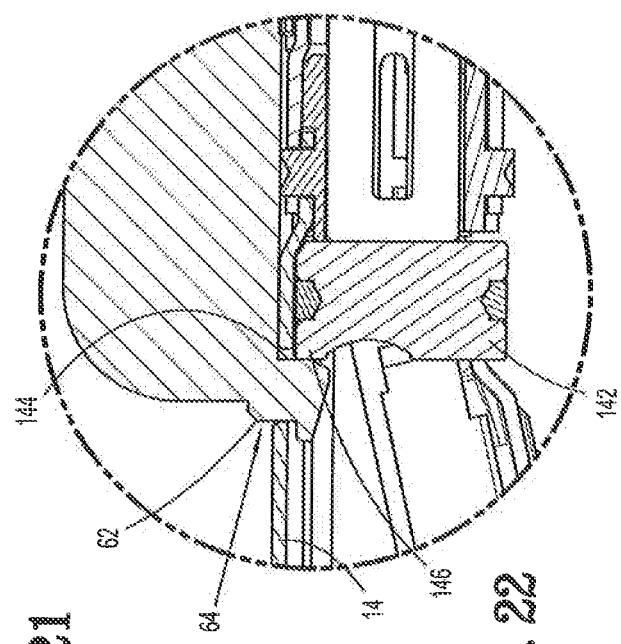
FIG. 22 is an enlarged area of detail view of FIG. 21 illustrating a distal shipping hook engaged with the SULU and blocking a knife blade of the SULU.

Referring finally to FIGS. 21 and 22, and as noted herein above, shipping wedge 10, and in particular distal hook 62 of shipping wedge 10, is provided to prevent inadvertent and premature movement or advancement of a knife blade 142 included in loading unit 12 distally within elongate tubular member 14. As best shown in FIG. 22, with distal hook 62 positioned through hole 64 in elongate tubular member 14, a proximal end 144 of distal hook 62 blocks distal movement of knife blade 142 by engagement with a distal end 146 of knife blade 142.

It will be understood that various modifications may be made to the embodiments disclosed herein. For example, the locking pin on the shipping wedge or loading lock may have alternative shapes, such as, for example T-shaped, etc. Further, the locking pin may be engaged by an edge of the locking plate. Additionally, the distal hook of the shipping wedge or loading lock may engage alternate components on the SULU such as, for example, driving bars for ejecting the staples, etc. The loading unit shown in FIG. 1 has a staple cartridge and an anvil. However, surgical instruments having staple cartridges that are removable and replaceable are also contemplated. Therefore, the above description should not be construed as limiting, but merely as exemplifications of particular embodiments. Those skilled in the art will envision other modifications within the scope and spirit of the claims appended hereto.

The invention claimed is:

1. A shipping wedge for use with a surgical instrument having a body portion, the shipping wedge comprising:
a base configured to be detachably secured with the body portion of the surgical instrument;
a blocking member depending from the base and engageable with a movable operative member of the surgical instrument; and
a locking member depending from the base and engageable with a lockout mechanism of the surgical instrument.

2. The shipping wedge according to claim 1, wherein the blocking member is a hook configured to engage with a knife member of the surgical instrument to inhibit movement of the knife member.

3. The shipping wedge according to claim 1, wherein the blocking member is pivotably associated with the body portion.

4. The shipping wedge according to claim 1, wherein the base includes a proximal end portion including the locking member and a distal end portion including the blocking member.

5. The shipping wedge according to claim 4, wherein the blocking member extends distally from the base.

6. The shipping wedge according to claim 1, wherein the locking member includes an enlarged flange.

7. The shipping wedge according to claim 6, wherein the flange is a circular disc.

8. The shipping wedge according to claim 7, wherein the shipping wedge includes a downward extension connecting the circular disc to the base.

9. The shipping wedge according to claim 8, wherein the circular disc has a diameter larger than a width of the downward extension.

10. The shipping wedge according to claim 1, further comprising flexible arms projecting from the base, wherein the flexible arms are shaped to cooperated with the body portion of the surgical instrument.

11. A surgical instrument comprising:
an elongate member;
a loading unit detachably coupled to the elongate member, the loading unit including:
a body portion;
a movable operative device disposed in the body portion; and
a lockout mechanism including a locking plate movably mounted to the body portion, the locking plate movable between a locked position and an unlocked position; and
a removable safety device including:
a blocking member engageable with the movable operative device; and
a lockout member engageable with the locking plate, wherein the removable safety device is locked to the body portion of the loading unit when the locking plate is in the locked position and is unlocked for removal from the body portion when the locking plate is in the unlocked position.

12. The surgical instrument according to claim 11, wherein the lockout member includes a neck portion and a flange portion extending from the neck portion.

13. The surgical instrument according to claim 12, wherein the locking plate includes a keyhole slot including a first portion configured to receive the flange portion of the lockout member and a second portion configured to receive the neck portion.

14. The surgical instrument according to claim 13, wherein the flange portion is a circular disc.

15. The surgical instrument according to claim 11, wherein the loading unit further includes a biasing member configured to bias the locking plate toward the locked position.

16. The surgical instrument according to claim 11, wherein the movable operative device is a knife member.

17. The surgical instrument according to claim 11, wherein the loading unit further includes an actuator configured to move the locking plate upon actuation of the actuator.

* * * * *